United States Patent [19]

Young

[11] Patent Number: 4,625,068

[45] Date of Patent: Nov. 25, 1986

[54] RHODIUM CATALYZED HYDROFORMYLATION OF INTERNAL OLEFINS

[75] Inventor: David A. Young, Baton Rouge, La.

[73] Assignee: Exxon Chemical Patents Inc., Florham Park, N.J.

[21] Appl. No.: 714,112

[22] Filed: Mar. 20, 1985

[51] Int. Cl.$^4$ .............................................. C07C 45/50
[52] U.S. Cl. .................................. 568/454; 568/902; 568/909
[58] Field of Search ................ 568/454, 909, 451, 902

[56] References Cited

U.S. PATENT DOCUMENTS

| | | | |
|---|---|---|---|
| 3,168,553 | 2/1965 | Slaugh | 568/454 |
| 3,239,566 | 3/1966 | Slaugh | 260/604 |
| 3,511,880 | 5/1970 | Booth | 260/604 |
| 3,527,809 | 9/1970 | Pruett et al. | 260/604 |
| 3,576,881 | 4/1971 | Senn, Jr. | 260/604 |
| 3,965,192 | 6/1976 | Booth | 260/598 |
| 4,195,052 | 3/1980 | Zuech | 568/454 |
| 4,201,728 | 5/1980 | Hughes | 568/454 |
| 4,221,744 | 9/1980 | Unruh | 568/454 |
| 4,277,627 | 7/1981 | Bryant et al. | 568/454 |
| 4,283,562 | 8/1981 | Billig et al. | 568/454 |
| 4,287,370 | 9/1981 | Harris et al. | 568/454 |
| 4,306,087 | 12/1981 | Matsumoto et al. | 568/454 |
| 4,443,638 | 4/1984 | Yates | 568/882 |

FOREIGN PATENT DOCUMENTS

| | | | |
|---|---|---|---|
| 762469 | 8/1971 | Belgium | 568/454 |
| 28378 | 5/1981 | European Pat. Off. | |
| 96988 | 12/1983 | European Pat. Off. | |

| | | |
|---|---|---|
| 1493154 | 8/1974 | United Kingdom . |

OTHER PUBLICATIONS

P. W. N. M. Van Leeuwen and C. F. Roobeck, J. Organomet. Chem., vol. 258, pp. 343-350 (1983).
B. Fell et al., Tetrahedron Letters, No. 29, pp. 3261-3266 (1968).
F. Asinger et al., I&EC Pro. Res. & Dev., vol. 8, No. 2, 214 (1969).
E. R. Tucci, I&EC Prod. Res. & Dev., vol. 8, No. 2, 215-26 (1969).
B. Fell et al., J. Molec. Catalysis, vol. 2, 211-218 (1977).
Van Leewen & Roobeck, J. Organomet. Chem., vol. 258, pp. 343-350 (1983).
A. A. Oswald et al., Preprint of Papers, American Chemical Society (Seattle Meeting, Mar. 20-25, 1983), vol. 2, No. 2, pp. 191-208.
R. L. Pruett et al., JO Chem., vol. 34, 327 (1969).
K. L. Oliver et al., Am. Chem. Soc. Pet. Div. Prepr. Gen. Pap., vol. 14, (3), A7 (1969).
C. A. Tolman, J. Amer. Chem. Soc., 92, 2953, 2956 (1970).
C. A. Tolman, J. Amer. Chem. Soc., 96, 53 (1974).
C. A. Tolman, Chem. Rev., vol. 77, No. 3, 313 (1977).

*Primary Examiner*—Werren B. Lone
*Attorney, Agent, or Firm*—J. B. Murray, Jr.

[57] ABSTRACT

Internal olefins are rapidly hydroformylated in high selectivity to aldehyde product using homogeneous rhodium catalysts modified with highly sterically hindered tricycloalkyl phosphine ligands under mild process conditions.

12 Claims, 1 Drawing Figure

RHODIUM CATALYZED HYDROFORMYLATION OF INTERNAL OLEFINS

BACKGROUND OF THE INVENTION

1. FIELD OF THE INVENTION

This invention relates generally to rhodium catalyzed hydroformylation of olefins and more specifically to an improved hydroformylation process for internal olefins using homogeneous rhodium catalyst systems containing highly sterically hindered tricycloalkyl phosphine ligands.

2. Description of the Prior Art

The hydroformylation of olefins to formaldehydes is a widely used industrial process in which an olefin, carbon monoxide and hydrogen, are reacted in the presence of a homogeneous hydroformylation catalyst. These catalysts have historically comprised high pressure cobalt systems. Recent developments of low pressure rhodium catalyst systems have been the subject of a considerable body of patent art and literature, and rhodium-triphenyl phosphine systems have been widely, and successfully, used commercially for the hydroformylation of propylene feedstocks to produce butyraldehyde.

A large variety of trialkyl phosphines have been suggested for use in rhodium catalyzed hydroformylation of olefins. U.S. Pat. No. 3,168,553 relates to the hydroformylation of olefins (including alpha and internal monoolefins and diolefins) using a Group VIIIb transition metal (Co, Ru, Rh and Ir) catalyst systems and triorganophosphorus ligands including trivalent phosphorus compounds having aliphatic, cycloaliphatic, heterocyclic and/or aromatic radicals satisfying the three valences of the trivalent phosphorus atom, at preferred carbon monoxide pressures of 5500 to 21,000 kPa (or higher) at temperatures of 75° to 250° C.

U.S. Pat. No. 3,239,566 also relates to the Rh and Ru catalyzed hydroformylations employing a tertiary organo-phosphine (e.g., trialkyl and tricycloalkyl phosphines, such as tricyclopentyl and tricyclohexyl phosphines) at 100° to 300° C. and total pressures of 690 to 13,800 kPa, using terminally- or internally-unsaturated olefins as feedstock.

U.S. Pat. No. 3,511,880 discloses the hydroformylation of alpha-olefins and internal-olefins employing a partially aqueous high boiling inert organic reaction medium containing a Group VIII noble metal biphyllic ligand complex as the catalyst and containing an alkaline material such as ammonium or alkali metal hydroxide. Suitable biphyllic ligands are said to include trialkyl phosphines, and tricyclohexyl phosphine and phenyldiisopropyl phosphine are disclosed as suitable. Reaction temperatures of 50° to 200° C., and reaction pressures of 100–30,400 kPa are employed. U.S. Pat. No. 3,965,192 is similar in its disclosure to U.S. Pat. No. 3,511,880, as to suitable triorgano phosphines.

U.S. Pat. No. 3,527,809 relates to a process for hydroformylation of alpha-olefins using triaryl phosphines (having a HNP value of at least 425) in combination with rhodium catalyst, at a total pressure of less than 3100 kPa and at temperatures of 50° to 145° C. Triisopropyl phosphine ligand is disclosed to be an unsuitable ligand due to its low HNP value. Also excluded were trialkyl phosphines and tricycloalkyl phosphines.

U.S. Pat. No. 4,201,728 discloses highly selective alpha-olefin hydroformylation catalysts comprising a stabilized rhodium complex containing a bidentate ligand and a monodendate ligand, which is characterized by cyclindrical cone angle $\theta$ of between about 135 and 150 degrees. The reactions are carried out at from 25° to 150° C. and at 103 to 20,700 kPa.

Internal olefins are known to be much less reactive than terminal olefins for hydroformylation. For example U.S. Pat. No. 4,221,744 (column 15, lines 40–60) indicates that the internal olefin is relatively inert under the conditions of all of its preceding examples, and the relative inertness of internal olefins is also taught in U.S. Pat. No. 4,287,370 under its conditions, in which a mixed butene feedstock is contacted with a rhodium triorganophosphine ligand system, in which the ligand can be trialkylphosphine (column 5, lines 29–30).

U.S. Pat. No. 3,576,881 (column 5, lines 20–23) teaches that biphyllic triorganophosphorus ligands having cycloaliphatic groups, do not form active catalyst species for Fe, Co and Rh catalyzed olefin hydroformylations. The reference, therefore, employs trialkyl and trialkoxy phosphorus ligands.

B. Fell et al., *Tetrahedron Letters* No. 29, pp. 3261–3266 (1968) conducted studies on olefin isomerizations during the hydroformylation of higher molecular weight olefins with complex cobalt and rhodium catalysts. Trialkyl phosphines were found to suppress olefin isomerization without suppressing hydroformylations, in hydroformylation of 1-octene and trans-octene-4 in an agitated autoclave at 20,270 kPa and 140° C. (using 1:1 $CO:H_2$) to greater than 90% theoretical yield, using $Rh_2O_3$ with either tricyclohexyl phosphine or tri-n-butyl phosphine (Table 2). N-hexenoic-3-acid-1-methyl ester was hydroformylated at 120° C. under similar conditions using a Rh catalyst system containing tricyclohexyl phosphine (Table 5). However, with four hours of reaction time, assuming complete conversion, the hydroformylation rates for tricyclohexyl phosphine (using a Rh concentration of 1.75 mmol Rh per mole of olefin charged) corresponded to a catalyst turnover of only 142.9 moles olefin/mole Rh/hour. Therefore, Fell et al. reported similar performance for tricyclohexyl phosphine and tri-n-butyl phosphine in Rh hydoformylation catalyst systems, no distinction in aldehyde production rates being observed. The Fell et al. experiments are also discussed in F. Asinger et al., *I&EC Prod. Res. & Dev.*, vol. 8, no. 2, 214 (1969) and E. R. Tucci, *I&EC Prod. Res. & Dev.*, vol. 8, no. 2, 215–26 (1969).

B. Fell et al., *J. Molec. Catalysis*, vol. 2, 211–218 (1977) investigated the hydroformylation of conjugated dienes using certain aliphatic tertiary phosphines (including tris-isopropyl phosphine) at specified conditions.

German Pat. No. 2,538,364, as abstracted in 85 Chem. Abs. 45,962m, reported no difference in results in the rhodium catalyzed hydroformylation of allyl alcohol with tris-triphenyl phosphine, tri-n-butyl phosphine, tricyclohexyl phosphine and 4-methyl benzene.

Van Leewen and Roobeek, *J. Organomet. Chem.*, vol. 258, pp. 343–350 (1983) investigated the hydroformylation of 2-alkyl-1-alkenes and cyclohexene with bulky phosphite ligands, and reported low rates of reaction when using tricyclohexyl phosphine as the ligand of the rhodium catalyst system.

U.S. Pat. No. 4,443,638 relates to a process for preparing alcohols from internal olefins including the step of hydroformylating internal olefins to aldehydes using a small amount of a recycled rhodium catalyst which is "ligand modified". Suitable ligands which are disclosed are the trialkylphosphites, tricycloalkyl phosphites, triarylphosphites, triarylphosphines, trialkyl phosphines, triarylstilbines and triaryl arsines. Temperatures of 145° to 180° C. and pressures of about 5,100 to 13,800 kPa are used in the hydroformylation. The recylced rhodium catalyst is separated from the hydroformylation reaction product by flash distillation, prior to the catalyst's recycle to the hydroformylation reactor.

European Patent Application 28,378 relates to an improved rhodium-catalyzed hydroformylation process wherein the catalyst stability is improved by use of a ligand selected from a branched chain alkyl diphenylphosphine, a branched chain dialkyl-phenylphosphine, a cycloalkyldiphenylphosphine, and a dicycloalkyl-phenylphosphine. European Patent Application No. 96,988 relates to a hydroformylation process for producing non-linear aldehydes from optionally substituted internal olefins, using a certain class of cyclic phosphite ligands.

A. A. Oswald et al., *Preprint of Papers, American Chemical Society* (Seattle Meeting, March 20–25, 1983), vol. 2, no. 2, pp. 191–208 reports the rhodium catalyzed hydroformylation of 1-butene using branched alkyl diphenyl phosphine ligands, including cyclohexyl diphenyl phosphine.

SUMMARY OF THE INVVENTION

It has been surprisingly found that internal olefins can be hydroformylated at a very rapid rate and in high selectivity to aldehyde product using a homogeneous rhodium catalyst system containing a highly sterically hindered tricycloalkyl phosphine ligand under mild process conditions.

The high rates of reaction achieved by the process of this invention are in excess of those which can be achieved by conventional rhodium triaryl phosphine catalyst systems which are thermally unstable at temperatures exceeding 145° C., and these rates are also surprisingly greatly in excess of those which can be achieved by use of tri-n-butyl phosphine under similar reaction conditions (contrary to the implications of B. Fell et al., *Tetrahedron Letters No.* 29, pp. 3261–3266 (1968)).

These catalyst systems are surprisingly stable at high temperatures, with negligible degradation rates being observed in continuous rhodium catalyzed hydroformylations.

The discovery that these tricycloalkyl phosphines provide such high rates of hydroformylation is especially surprising since they are generally strong Lewis Bases, and from the prior art would be expected to give lower rates of reaction, since the phosphorus-rhodium bond strength is known to increase with increasing Lewis basicity of the phosphine ligand. The resulting ligand is therefore less labile and the Rh complex should, therefore, be expected to be less active. In contrast, it has been found that the rhodium-tricycloalkyl phosphine catalysts of this invention are more active under the reaction conditions disclosed herein than are rhodium tri-n-alkyl phosphines, even though tri-cyclohexyl phosphine is a more basic ligand.

It is theorized, without being bound thereby, that the sterically hindered tricycloalkyl phosphine ligands of this invention enable fundamental changes in catalyst structure to be maintained in the reaction medium, as a result of the steric crowding of the bulky phosphine ligands. The net result is that these catalysts have fewer phosphines and more carbon monoxide bound to the rhodium in the active form than do catalysts with smaller, less crowded phosphine ligands.

My findings regarding the increased rates are also contrary to the understanding of the prior art which qualitatively show that both rate and selectivity increase as the phosphine ligand is changed from a more basic alkyl phosphine to the less basic aryl phosphine. R. L. Pruett et al., *JO Chem*, vol. 34, 327 (1969); K. L. Oliver et al., *Am..Chem. Soc. Pet. Div. Prepr, Gen. Pap.*, vol. 14 (3), 47 (1969).

It has been further found that an increased hydrogen partial pressure has an activating, and hence beneficial effect on the catalyst system. In contrast, it has been taught that hydrogen partial pressures should be controlled to minimize unnecessary loss of excess hydrogen without any attended benefit (U.S. Pat. No. 4,287,370). Also, activity has been found to be proportional to the total carbon monoxide and hydrogen pressure and has also surprisingly been found to be relatively independent of phosphine ligand concentration or phosphorus:-rhouium molar ratios, again contrary to teachings in the prior art.

The bulky tricycloalkyl phosphines of this invention have been further found to exhibit a hydroformylation reaction rate which is essentially independent of ligand to Rh moluar ratio (over the tested range from 15:1 to 80:1) and a less than first order dependence upon Rh concentration was observed.

DETAILED DESCRIPTION OF THE INVENTION

Figure 1:
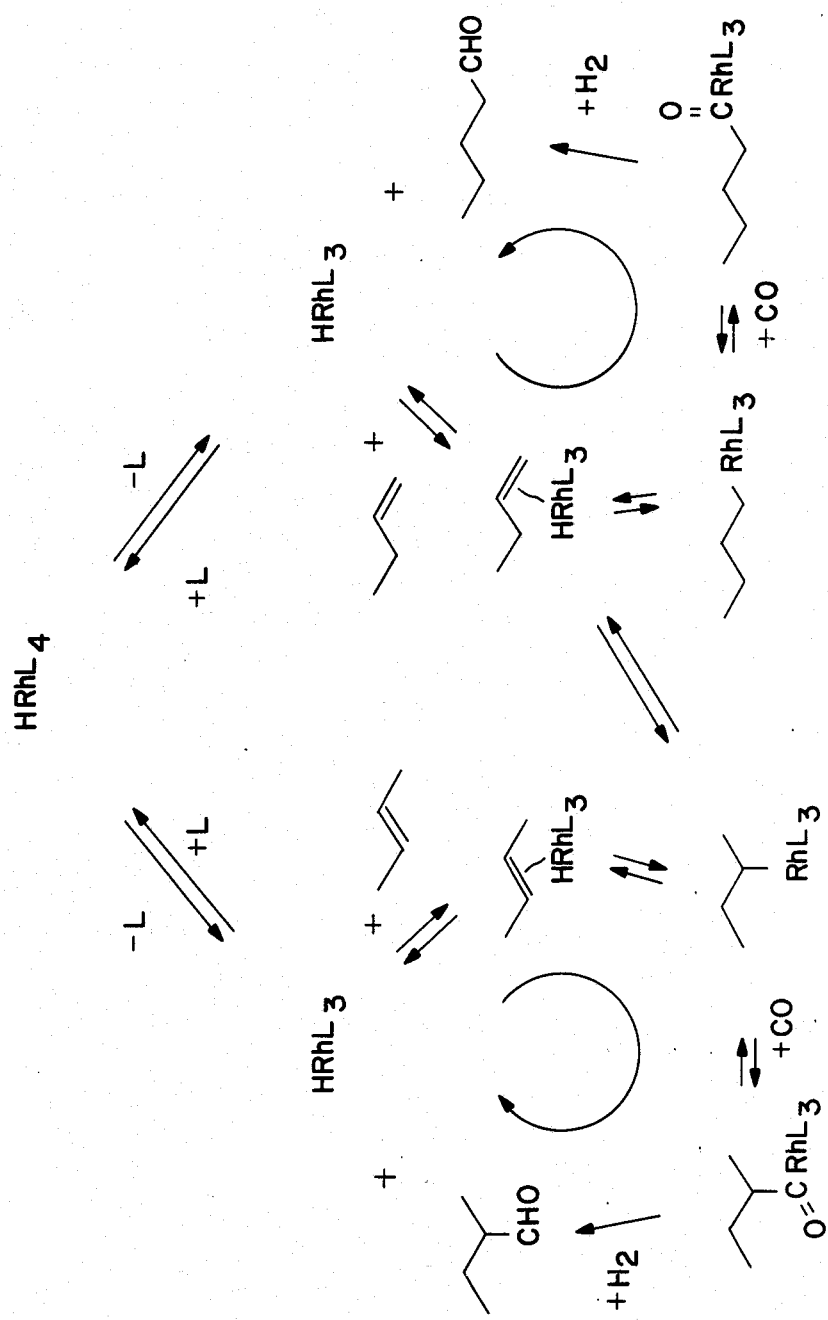
FIG. 1 is an illustration of the abbreviated reaction mechanism of homogeneous rhodium oxo catalyst complexes.

The olefins which are passed as feedstocks to the process of this invention contain internal carboncarbon double bonds and can comprise members selected from the group consisting of aliphatic olefins, cycloaliphatic olefins, and substituted derivatives thereof wherein the substituent comprises alkyl, aryl, alkaryl, aralkyl, cycloalkyl, hydroxy, —CHO, carboxylate (—C(O)OX, wherein X is alkyl of 1 to 20 carbon atoms) and the like. Also useful are ethers of unsaturated alcohols and esters of unsaturated alcohols and/or acids. A preferred class of internal olefins are internal aliphatic olefins having from 4 to 20 carbon atoms per molecule, cycloaliphatic olefins having from 3 to 12 carbon atoms per molecule, and alkyl and aryl substituted derivatives of the foregoing wherein the alkyl substituent contains from 1 to 17 carbon atoms and the aryl substituent contains from 6 to 10 carbon atoms. Especially preferred are internal olefins wherein at least one of the carbon atoms $<C=O>$ are substituted by one hydrogen tom (e.g., 2-butene, and 2-methyl-2-butene). Illustrative of suitable internal aliphatic olefins are straight and branched chain alkenes, such as cis- and trans-butene-2, 2-pentene, 2-hexene, 3-hexene, 2- and 3-heptene, 2-, 3-, and 4-octene, 2,4,4-trimethyl-2-pentene, 2-methyl-2-butene, 3-methyl-2-heptene, 3,4-dimethylhexene-2, decene-2, 4-amyldecene-2, and the like. Illustrative of suitable cycloaliphatic olefins are cyclopropene, cyclobutene, cyclopentene, cyclohexene, cycloheptene, cyclooctene, cyclodecene, cyclodedecene, 1,5-cyclooctadiene, dicyclopentadiene, 4-vinyl-1-cyclohexene, bicyclo-[2.2.1] hepta-2, 5-diene and the like. Illustrative of suitable alkyl and aromatic substituted derivatives of the foregoing include 1-phenyl-1-propene, cis- and trans-stilbene, diethyl maleate, diethyl fumarate, crotonaldehyde, crotonaldehyde, dimethyl acetal, ethyl cinnamate, prop-1-enyl t-butyl ether, and methyl, ethyl and butyl esters of acrylic acid. methacrylic acid, oleaic acid and linoleic acid, methyl crotonate, and the like.

The internal olefin may be supplied to the hydroformylation zone in substantially pure form, or as a mixture with one or more alpha-olefins and/or inert materials such as saturated hydrocarbons, nitrogen, argon, and carbon dioxide. In mixtures containing one or more alpha olefins, the internal olefin is the major component. The saturated hydrocarbons will generally comprise hydrogenation by-products of the hydroformylation reaction, for example normal-butane in the case of hydroformylation of butene-2. Where present, the alpha-olefin will generally be employed in the amount of less than about 15 wt. %, and more generally less than about 5 wt. %.

As an example of a mixed internal/alpha-olefin stream, there may be mentioned the use of a mixed C4 hydrocarbon feedstock containing cis- and trans-butene-2, butene-1, iso-butylene, normal-butane, iso-butane and minor amounts of $C_{1-5}$ alkanes. In this instance, the alpha-olefins butene-1 and iso-butylene will be converted into the corresponding aldehydes, that is mainly normal-valeraldehydes and 3-methylbutyraldehyde respectively. In such a mixed hydrocarbon feedstocks, again, the major olefin component usually internal olefin, e.g., butene-2.

The tricycloalkyl phosphine ligands ("L") which are employed in the process of the invention comprise ligands of the formula:

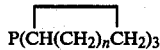 (I)

wherein "n" is an integer of 1–12, inclusive.

Exemplary ligand of formula (I) are tri-cyclopropylphosphine, tri-cyclobtylphosphine, tri-cyclopentylphosphine, tri-cyclohexylphosphine, tri-cycloheptylphosphine, tri-cyclooctylphosphine, tri-cyclononylphosphine, tri-cyclodecylphosphine, tri-cyclododecylphosphine and the like.

The preferred ligands are members selected from the group consisting of the following formula:

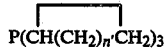 (II)

wherein n' is an integer of from 1 to 8, inclusive. Illustrative of such preferred ligands are tri-cyclohexyl phosphine, tri-cyclooctyl phosphine, tri-cyclopentyl phosphine and the like.

It is an important aspect of the present invention hydroformylation catalyst system that the ligand component is employed in a molar excess, and that the ligand has an atomic structure with a specific steric configuration in the stabilized catalyst complex, i.e., the steric parameter $\theta$ of the ligand in the catalyst complex is an apex of least 145°, preferably from 165° to 170°, and most preferably about 170°. By the term "steric parameter $\theta$" is meant the apex angle of a cylindrical cone, centered 2.28 Å from the center of the group VA atom Q', which just touches the Van der Waals radii of the outermost atoms of the R' substituents of a symmetrical Q'R'$_3$ ligand [C. A. Tolman, J. Amer. Chem. Soc., 92, 2953 (1970); Ibid, 92, 2956 (1970); and Ibid, 96, 53 (1974); C. A. Tolman, Chem. Rev., vol. 77, no. 3, 313 (1977)].

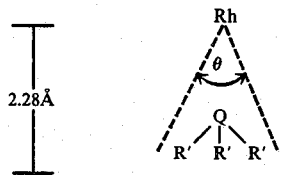

The steric parameters $\theta$ apex angle of an unsymmetrical ligand (e.g., Q'R$^1$R$^2$R$^3$, where R$^1$, R$^2$ and R$^3$ are different hydrocarbyl groups) can be estimated from a knowledge of the cone angles of the corresponding symmetrical ligands Q'(R$^1$)3, Q'(R$^2$)3 and Q'(R$^3$)3, on the basis of the formula:

$$\theta(Q'R'R^2R^3) = \frac{2}{3} \left[ \frac{\theta(Q^1R^1)_3}{2} + \frac{\theta[Q^1(R^2)_3}{2} + \frac{\theta[Q^1(R^3)_3}{2} \right] \quad \text{(III)}$$

Catalyst Preparation

The present invention's catalysts can be prepared in situ in the hydroformylation reaction zone or, alternatively, can be prepared ex-situ and subsequently introduced into the reaction zone with the appropriate hydroformylation reactants. The most preferred catalysts are prepared by admixing one mole of suitable rhodium source with between about 10 to 100 moles of ligands L.

The amount of processing required for conversion of the rhodium metal depends on the nature of the initial rhodium source. Hence, if the rhodium in the starting material source is a salt in which rhodium is the cation moiety (e.g., a Rh$^{+3}$ valence state), at some stage in the catalyst preparation or in the hydroformylation process the rhodium metal must be reduced to the Rh$^{+1}$ valence state. The reduction is normally accomplished with hydrogen, or other reducing agents. When the rhodium source compound contains halogen, then a halide scavenger is employed in connection with the rhodium valence state reduction so as to eliminate the hydrogen halide as it is generated during the reduction step. This can be achieved by contact with H$_2$/CO in the hydroformylation process, or alternatively by employment of an equivalent source of hydrogen such as hydride (e.g., sodium borohydride).

In a preferred method of catalyst preparation, the rhodium source compound (e.g., a rhodium salt of a mineral acid or a carboxylic acid) is converted to a carbonyl derivative in a first step, followed by subsequent reaction of a rhodium carbonyl derivative with the ligands. If the primary rhodium source compound is already a carbonyl-containing compound then the initial carbonylation step can be eliminated.

Suitable rhodium sources which do not already comprise a carbonyl moiety in the molecule include the simple salts such as the halides (especially rhodium trichloride trihydrate), rhodium sulfate, rhodium nitrate, and rhodium carboxylates including the rhodium salts of simple carboxylic acids and dicarboxylic acids. Rhodium sources already containing carbonyl moiety in the molecule include (PPh$_3$)$_3$Rh(CO)H, (PPh$_3$)$_2$Rh(CO)Cl, Rh$_6$(CO)$_{16}$, Rh[CO]$_2$AcAc (rhodium dicarbonyl acetyl acetonate) and rhodium carbonyl chloride dimer (i.e., [Rh(CO$_2$)Cl]$_2$. The material known in the trade as "rhodium on carbon", which comprises a mixture of rhodium oxides of a rather complex nature on a carbon support, can also be employed hydridocarbonyltris (triphenylphosphine) rhodium (I) is a highly preferred rhodium source for catalyst preparations.

The various methods of preparing the present invention ligand stabilized rhodium catalysts can be summarized as follows:

(1) When the rhodium is initially in a noncarbonyl form, the rhodium is converted to a carbonyl derivative by reaction with carbon monoxide. Typical carbonylation procedures are described in "Inorganic Synthesis", vol. 8, 211 (1966).

The rhodium carbonyl compound is then combined with the ligand and component of the catalyst system.

If hydrogen halide is generated during the catalyst preparation, a base is added as a halide scavenger. Alkaline borohydride is a versatile reagent for rhodium valence state reduction from $Rh^{+3}$ to $Rh^{+1}$, and for concomitant halide scavenging.

(2) When rhodium is initially available in the form of a carbonyl derivative, the rhodium carbonyl compound is reacted directly with the ligand to form the ligand stabilized rhodium catalyst. When the rhodium carbonyl derivative is a compound such as rhodium carbonyl chloride dimer, the interaction with the ligand is conducted in the presence of (1) a hydrogen chloride scavenger such as pyridine or sodium hydroxide, and (2) a hydride source such as hydrogen or a borohydride.

(3) Another alternative which is a convenient laboratory procedure is to form the rhodium carbonyl hydride by displacing triarylphosphine ligands from hydridocarbonyltris (triphenylphosphine) rhodium (I) with ligand:

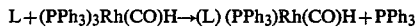
$L+(PPh_3)_3Rh(CO)H \rightarrow (L)(PPh_3)Rh(CO)H + PPh_3$

This produces a complex with L as the ligand. In order to shift the equilibrium to increase the displacement of $PPh_3$, it is usually required to incorporate in the reaction medium an excess of ligand, e.g., 10 to 100 moles of L per mole of rhodium metal in the complex.

The catalyst preparation procedures described above are all conducted in the liquid phase and preferably in the presence of an inert solvent such as benzene or toluene. Suitable reaction temperatures are in the range between about 25° and 100° C.

Hydroformylation Conditions

As a general procedure, the catalyst system is first formed in a deoxygenated solvent medium in a hydroformylation reaction zone is a manner as described above. Excess ligand can perform as the solvent medium. The hydroformylation zone is pressured with hydrogen and carbon monoxide and heated to a selected reaction temperature. Interal olefin feed is then charged to the hydroformylation zone, and the reaction is conducted until the desired conversion yield and efficiency have been attained. the reaction can be performed in a batchwise, continuous or semi-continuous manner.

It is preferred that the temperature of the hydroformylation reaction be maintained in the range between about 80° and 200° C. For most of the internal olefin hydroformylation reactions, a reaction temperature between about 120° and 180° C. and a reaction time between about 0.5 and 4 hours is particularly preferred.

The pressure in the hydroformylation reaction zone is important to obtain the observed high rates of reaction, and the maximum pressure generally will be less than about 14,000 kPa to avoid increased expenses in pressure resistant equipment. Preferably, a total pressure within the range of from about 3,500 to 14,000 kPa, and more preferably from about 5,500 to 11,000 kPa, will be used.

The ratio of hydrogen to carbon monoxide can vary broadly over a mole ratio range between about 0.2:1 and 5:1. The average mole ratio will vary between about 0.5:1 and 2:1. The quantity of hydrogen/carbon monoxide charged should be at least sufficient to satisfy the stoichiometric requirements of the internal olefin hydroformylation system.

Although it is not essential, an inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes; halogenated aromatics including orthodichlorobenzene; ethers such as tetrahydrofuran, dimethoxyethane and dioxane; halogenated paraffins including methylene chloride; paraffinic hydrocarbons such as heptane; and the like.

It is an important aspect of the present invention that the hydroformylation process is conducted in the presence of excess ligand, and that the ligand component of the ligand stabilized catalyst has a steric parameter $\theta$ apex angle of from about 165° to 170°, and most preferably from about 160° to 170°, in order to achieve optimum advantages in the practice of the invention process, i.e., highly selective and efficient conversion of internal olefins to ensure sufficient ligand to overcome loss of ligand due to poisoning by trace impurities (such as $O_2$, S or halides), and to provide sufficient thermal stability to the catalyst to avoid plating out of Rh metal on equipment surfaces, particularly in catalyst recycle lines.

The sterically hindered ligands employed in this invention are provided in the hydroformylation medium in a mole ratio of between about 10 to 100 moles, preferably between about 15 and 80 moles, of the ligand per gram atom of rhodium metal. The rhodium concentratrion in the liquid reaction medium may vary from about 10 ppm or less up to about 1,000 ppm or more, calculated in each case as rhodium metal and on a weight-/volume basis. Typically, the rhodium concentration in the liquid reaction medium lies in the range of from about 40 ppm up to about 200 ppm, calculated as rhodium metal. For economic reasons, it will not usually be desirable to exceed about 500 ppm rhodium, calculated as metal, in the liquid reaction medium.

Without intending to by bound thereby, it is believed that complexed rhodium-catalyzed homogeneous hydroformylations involve a reaction mechanism in which the predominant form of the catalyst present under hydroformylation conditions, the catalyst reservoir, is a five coordinate Rh species such as complex VI, VII or VIII illustrated below, wherein "L" represents a triorganophosphine ligand. Complexes I and II have been reported observed directy by $^{31}P$ NMR spectroscopy under hydroformylation conditions with tristriphenylphosphine as ligand.

It has been postulated that the rate determining step for this hydroformylation reaction in the generation of four coordinate unsaturated complexes such as IX or X. Moreover, it was postulated that under conditions of high triphenyl phosphine concentrations, complex IX gives high selectivity to linear aldehyde product using alpha-olefin feeds, an that complex X is much less selective for linear aldehyde, versus branched aldehyde products.

It is believed that the precise form of the rhodium-complex in the hydroformylation reaction medium varies and its equilibrium can be illustrated as follows wherein again "L" is a tri-organophosphine ligand.

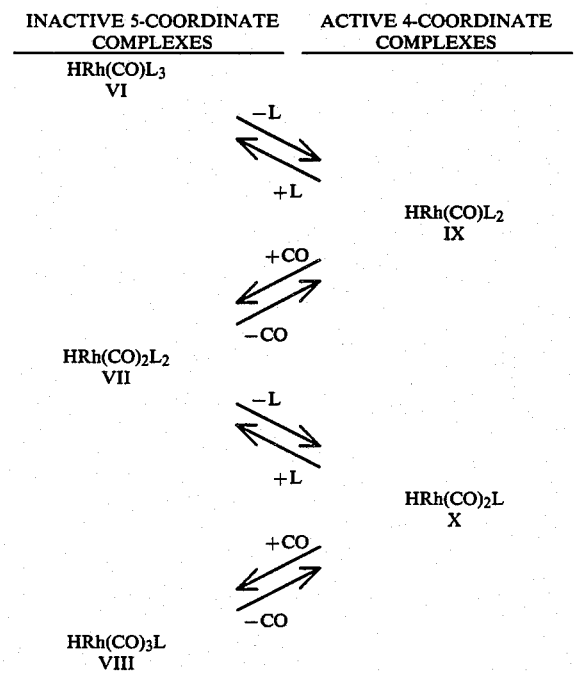

| INACTIVE 5-COORDINATE COMPLEXES | ACTIVE 4-COORDINATE COMPLEXES |
|---|---|
| HRh(CO)L$_3$ VI | |
| | HRh(CO)L$_2$ IX |
| HRh(CO)$_2$L$_2$ VII | |
| | HRh(CO)$_2$L X |
| HRh(CO)$_3$L VIII | |

The relative predomination of a given rhodium complex VI-X is believed to be dependant upon a large variety of variables, namely, temperature, CO partial pressure, H$_2$ partial pressure, total reaction pressure, "L" ligand concentration and Lewis basicity of the ligand and steric size ($\theta$ cone angle 1 of the ligand). The lubility of the "L" ligand, and thus the catalyst activity, is a function of the strength of the L—Rh bond, which is a function in itself of the Lewis basicity and the steric size of L. It has been found that increasing temperature or increasing CO pressure shifts the complex away from VI toward VIII and that oxo reaction rate increases as the complex is shifted from VI toward VIII. Also, increased CO and H$_2$ total pressures causes an increased stability of the rhodium complex as the complex is moved in the direction of VIII. In contrast, increased L concentration leads to a shift away from complex VIII toward complex VI, and results in an increase in the normal-to-iso isomer ratio in the product aldehyde with alpha-olefins.

The VI-VIII complexes are illustrated by the well known triphenyl phosphine-rhodium hydroformylation catalyst system (U.S. Pat. No. 3,527,809), which is commercially employed for linear alpha-olefin hydroformylations to form linear aldehydes.

Since reaction variables that give high n/i product from butene-1, i.e., reaction variables, that destabilize branched vs. linear intermediate complexes as in the catalyst cycle should also produce slow rates of butene-2 hydroformylation. Thus, the observed relative inactivity of butene-2 hydroformylation with conventional catalyst systems can be readily explained.

It can be seen that, to a large degree, the precise balancing of temperature, pressures and other reaction parameters is important to reaction rate, reaction selectivity and, importantly, to catalyst stability.

It has been surprisingly found that the bulky phosphine ligands of this invention, under the reaction conditions herein described emphasize the mono-phosphine bis-carbonyl rhodium hydride, HRh(CO)$_2$L (i.e., complex X), over the bis-phosphine mono-carbonyl rhodium hydride (i.e., HRh(CO)L$_2$, or complex IX) and that this form (X) of the rhodium catalyst is stable at high temperatures and elevated pressures, and catalyzes the hydroformylation of internal olefins at very rapid rates.

In conventional Rh-triarylphosphine hydroformylation catalyst systems, increased CO partial pressure has an inhibiting effect on the oxo reaction rate, whereas increased H$_2$ partial pressure has an activating effect. These opposing effects result in a balance which, at a given CO:H$_2$ molar ratio (required to maintain oxo stoichiometry tend to cancel one another out. In contrast, the bulky ligands of this invention have been surprisingly found to permit use of increased CO partial pressures as well as increased H$_2$ partial pressures without the attendant, conventional deactivation of the catalyst.

The amount of olefin fed to the reaction mixture depends on several factors, size of the reactor, the temperature of reaction, the total pressure, the amount of catalyst, etc. In general, the higher the olefin concentration is in the reaction medium, the lower usually will be the catalyst concentration that can be used to achieve a given conversion rate to aldehyde products in a given size of reactor. Since partial pressures and concentration are related, the use of higher olefin partial pressure leads to an increased proportion of the olefin in the product stream leaving the reaction mixture. Further, since some amount of saturated hydrocarbon may be formed by hydrogenation of the olefin, it may be necessary to purge part of the product gas stream in order to remove this saturated product before any recycle to the reaction zone, and this would be a source of loss for the unreacted olefin contained in the product gas stream. Hence, it is necessary to balance the economic value of the olefin lost in such a purge stream against the economic savings associated with lower catalyst concentration.

The aldehyde and alcohol products can be recovered from the reaction liquid by conventional means, as by distillation, gas stripping, flashing and the like, and the separated liquid catalyst mixture can be recycled to the hydroformylation reaction zone, along with make-up CO, H$_2$ and olefin (and make-up Rh and/or ligand as required).

Alternatively, the aldehyde and alcohol products can be removed as vapors from the hydroformylation reaction zone, condensed and treated for separation and purification using conventional procedure. Such a product flash off process alternative is known and is more fully described in U.S. Pat. No. 4,277,627, the disclosure of which is hereby incorporated by reference. If desired, the recovered aldehyde(s) can be conventionally hydrogenated (optionally after aldolization to form the corresponding dimer aldehyde(s)) to the alcohol, which in turn, can be purified using conventional technology and employed to esterify phthalic or other anhydrides to form plasticizers.

The make-up gases fed to the reaction medium will generally comprise the olefin, carbon monoxide, and hydrogen. Extrinsic poisons such as sulfur and sulfur-containing compounds, as well as halogens and halogen containing compounds, and the like, should be excluded from the make-up gases, since such materials can poison the catalyst and can deactivate the catalyst rather rapidly. Hence, it is desirable to reduce the amount of such poisons in all gases fed to the reaction. Of course, the amount of such poisons that can be tolerated is determined by the maximum acceptable rate of loss of activity of the catalyst, discussed above. If it is possible to permit some small amount of such poisons and still obtain a catalyst of desired stability, then such small amounts can be tolerated. It is generally desirable to reduce the amounts of such poisons in the make-up gases to below one part per million. This can be accomplished by methods known in the art.

The time of reaction, or residence period of the olefin in the reaction zone, is generally that time which is sufficient to hydroformylate the internal ethylenic bond of the alpha-olefin. As a general rule, the residence period in the reaction zone can vary from about several minutes to about several hours in duration and as is apparent, this variable will be influenced, to a certain extent by the reaction temperature, the choice of internal olefin and catalyst, the concentration of free ligand, the total pressure, the partial pressure exerted by carbon monoxide and hydrogen, the conversion rate and other factors. As a general rule, it is desirable to achieve the highest possible conversion rate for the smallest amount of catalyst employed. Of course, the ultimate determination of a conversion rate is influenced by many factors including the economics of the process. A substantial advantage of the present invention is that catalyst deactivation is minimized or substantially prevented while obtaining excellent conversion rates over prolonged periods of time.

The improved process of this invention can be further illustrated by reference to the following examples, wherein parts are by weight unless otherwise indicated.

EXAMPLE 1

A series of runs were performed in which the selected amount of rhodium dicarbonyl acetylacetonate and 2,2,4-trimethyl-1,3-pentane diol monoisobutyrate as a solvent (120.0 grams) and the selected amount of a triorganophosphine ligand were charged to a 300 cc stainless steel autoclave equipped with a stirrer under nitrogen atmosphere (10 psig) after which the autoclave was sealed and heated to the desired reaction temperature with stirring. At the reaction temperature, 30.0 grams of 2-butene was charged to the autoclave, the pressure was increased to the desired reaction pressure using a 1:1 $CO:H_2$ vol:vol ratio gas mixture. The reaction pressure was maintained by continuous addition of addition of the $CO/H_2$ gas mixture. After 2 minutes, a sample was withdrawn and the product concentrations were determined by gas chromatography analysis. After 15, 30, 60, 120 and 180 minutes samples were also withdrawn and so analyzed. The products consisted of 2-methyl butyraldehyde 2-methyl butanol, n-valeraldehyde, n-pentanol and traces of 1-butene and butane. The data thereby obtained are summarized in Table 1 below.

TABLE I

| Run No. | Phosphine Ligand (L) | [L] Mx $10^{-3}$ | Cone Angle $\theta$ | Reaction Temp. °C. | Reaction Press. kPa | First Order Rate Constant k, $min^{-1}$ Observed (1) | Olefin Turnovers/ min. (2) | First Order Reaction ½ Life (min.) | n/i Aldehyde Molar Ratio | % Alcohols in Total Product (4) |
|---|---|---|---|---|---|---|---|---|---|---|
| 1-1 | $P(CH_3)_3$ | 5.425 | 118 | 160 | 8270 | 0.096 | 12.3 | 7.2 | (100% i) | 45.0 |
| 1-2 | $P(n-butyl)_3$ | 5.425 | 132 | 160 | 1200 | 0.216 | 27.8 | 3.21 | 0.25 | 33.0 |
| 1-3 | $P(iso-butyl)_3$ | 5.425 | 143 | 160 | 8270 | 0.183 | 23.5 | 3.79 | 0.59 | — |
| 1-4 | $P(iso-propyl)_3$ | 5.425 | 160 | 160 | 8270 | 0.315 | 40.5 | 2.20 | 0.54 | 58.7 |
| 1-5 | $P(sec-butyl)_3$ | 5.425 | 160 | 160 | 8270 | 0.385 | 49.5 | 1.80 | 0.76 | 7.7 |
| 1-6 | $P(CH(CH_2)_4CH_2)_3$ | 5.425 | 170 | 160 | 8270 | 0.408 | 52.4 | 1.70 | 0.52 | 52.0 |
| 1-7 | $P(tert-butyl)_3$ | 5.425 | 182 | 160 | 8270 | 0 | — | — | — | — |
| 1-8 | $P(C_6H_5)_3$ | 5.425 | 145 | 160 | 8270 | 128 (3) | — | — | 1.05 | — |
| 1-9 | $P(C_6H_5)_3$ | 5.425 | 145 | 110 | 2410 | 42 | 1.8 | 49.51 | 0.45 | 0 |

(1) Rates are first order appearance of combined (n + i) aldehyde + alcohol in $min^{-1}$ Rh molal concentration of 0.33 millimolal (0.050 millimole Rh catalyst, calculated as Rh metal charged).
(2) Moles of olefin reacted per mole Rh per second in first ½ life of the reaction.
(3) Triphenyl phosphine decomposition was observed.
(4) Wt. % alcohol of total aldehyde and alcohol at >90% conversions.
[All tests using a P/Rh molar ratio = 50:1.]

EXAMPLE 2

A series of additional runs were made using tris-tricyclohexyl phosphine, employing the experimental procedure of Example 1. The data thereby obtained are set forth in Table II.

TABLE II

| Run No. | Phosphine Ligand (L) | [L] Mx $10^{-3}$ | P/Rh mole Ratio | Reaction Temp. °C. | Reaction Press. kPa | First Order Rate Constant k, $min^{-1}$ Observed (1) | Olefin Turnovers/ min (2) | First Order Reaction ½ Life (min.) | n/i Aldehyde Molar Ratio | % Alcohols in Total Product (3) |
|---|---|---|---|---|---|---|---|---|---|---|
| 1-8 | $P(CH(CH_2)_4CH_2)_3$ | 5.425 | 50:1 | 160 | 8270 | 0.408 | 1.7 | 52.4 | 0.52 | 7.9 |
| 2-1 | " | 5.425 | 50:1 | 160 | 8270 | 0.112 | 6.2 | 14.4 | — | — |
| 2-2 | " | 5.425 | 50:1 | 110 | 2070 | 0.012 | 57.8 | 1.5 | 0.2 | Trace |

TABLE II-continued

| Run No. | Phosphine Ligand (L) | [L] Mx $10^{-3}$ | P/Rh mole Ratio | Reaction Temp. °C. | Reaction Press. kPa | First Order Rate Constant k, min$^{-1}$ Observed (1) | Olefin Turnovers/ min (2) | First Order Reaction ½ Life (min.) | n/i Aldehyde Molar Ratio | % Alcohols in Total Product (3) |
|---|---|---|---|---|---|---|---|---|---|---|
| 2-3 | " | 5.425 | 50:1 | 110 | 8270 | 0.020 | 34.7 | 2.6 | 0 | Trace |
| 2-4 | " | 5.425 | 1:1 | 160 | 8270 | 0.407 | 1.7 | 52.4 | 0 | Trace |
| 2-5 | " | 5.425 | 100:1 | 160 | 8270 | 0.289 | 2/4 | 37.1 | — | — |

(1) Rates are first order appearance of combined (n + i) aldehyde + alcohol in min$^{-1}$ Rh molal concentration of 0.33 millimolal (0.050 millimole Rh catalyst, calculated as Rh metal charged).
(2) Moles of olefin reacted per mole Rh per second in first ½ life of the reaction.
(3) Wt. % alcohol of total aldehyde and alcohol at >90% conversions.

EXAMPLE 3

The procedure of Example 1 (Run 1–8) was repeated except that 90 grams of 2,2,4-trimethyl-1,3-pentanediol monoisobutyrate was used as solvent and trans-4-octene (60.0 grams) were charged to the autoclave as the olefin, to provide a Rh concentration of 0.33 molal Rh. The olefin was hydroformylated in the rhodium-tricyclohexylphosphine catalyst system at 160° C., 8270 kPa (CO:H$_2$=1:1) and the rate constant was found to be 0.146 (min$^{-1}$) with a 0.23 n/i aldehyde ratio of the 2-propyl hexanal and 3-ethyl heptanal products, with the formation of 12.5% alcohols, based on the total aldehyde and alcohol in the product. This provided a first order reaction half-life of 4.8 minutes.

The above rates of reaction indicate that substantially complete conversion (e.g., at 97% conversion, calculated at 5 half-lives) will occur using the above catalyst-ligand system at about 24 minutes of reaction (5×4.8 min.) under the above conditions.

It will be obvious that various changes and modifications may be made without departing from the invention and it is intended, therefore, that all matter contained in the foregoing description shall be interpreted as illustrative only and not limitative of the invention.

What is claimed is:

1. In a process for hydroformylation of an internal olefin selected from the group consisting of aliphatic olefins, cycloaliphatic olefins, and substituted derivatives thereof wherein the substituent comprises alkyl, aryl, alkaryl, aralkyl, cycloalkyl, hydroxy, —CHO and —C(O)OX, where X is alkyl of 1 to 20 carbon atoms in a hydroformylation reaction zone in the presence of a liquid rhodium triorgano phosphine catalyst system and in the presence of carbon monoxide and hydrgoen to form the corresponding aldehydes, the improvement which comprises employing in the reaction zone at least one sterically hindered tricycloalkylphosphine selected from the group consisting of compounds having the formula:

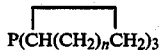

wherein "n" is an integer of 1–12, inclusive; and maintaining in the reaction zone a reaction temperature of from about 80° to 200° C., and a total carbon monoxide and hydrogen pressure of from about 3500 to 14,000 kPa, whereby improved hydroformylation reaction rates are achieved.

2. The improved process of claim 1 wherein said tricycloalkylphosphine comprises compounds of the formula

wherein "n'" is an integer of 1–8, inclusive.

3. The improved process of claim 1 wherein a temperature of from 120° to 180° C. and a pressure of from about 5,500 to 11,000 kPa is maintained in said reaction zone.

4. The improved process of claim 3 wherein said ligand is tricyclohexylphosphine.

5. The improved process of claim 1 wherein the mole ratio of H$_2$ to CO in the reaction zone is between about 0.2:1 and 5:1.

6. The improved process of claim 1 wherein the tricycloalkyl phosphine is employed in an amount sufficient to provide from about 10 to 100 moles of said tricycloalkyl phosphine per gram atom of rhodium in said reaction zone.

7. A process for hydroformylation of an internal olefin to form the corresponding aldehyde which comprises contacting an internal olefin selected from the group consisting of aliphatic olefins, cycloaliphatic olefins, and substituted derivatives thereof wherein the substituent comprises alkyl, aryl, alkaryl, aralkyl, cycloalkyl, hydroxy, -CHO or -C(O)OX, wherein X is alkyl of 1 to 20 carbon atoms in a hydroformylation reaction zone in the presence of H$_2$ and CO and in the presence of a liquid reaction medium containing a rhodium organophosphine hydroformylation catalyst wherein said organophosphine comprises at least one tricycloalkylphosphine of the formula:

wherein "n" is an integer of 1 to 8, inclusive, and maintaining in the reaction zone a total carbon monoxide and hydrogen pressure of from about 3,500 to 14,000 kPa and a reaction temperature of from about 80° to 200° C.

8. The process according to claim 7 wherein said internal olefin comprises at least one member selected form the group consisting of internal aliphatic olefins having from 4 to 20 carbon atoms per molecule, cycloaliphatic olefins having 3 to 12 carbon atoms per molecule, and alkyl and aryl substituted derivatives of the foregoing wherein the alkyl substituent contains from 1 to 17 carbon atoms and the aryl substituent contains from 6 to 10 carbon atoms.

9. The process according to claim: 8 wherein said tricycloalkylphosphine comprises tricyclohexyl phosphine, tri-cyclooctyl phosphine or tricyclopentyl phosphine.

10. The process according to claim 7 wherein said tricycloalkyl phosphine ligand is employed in said liquid reaction medium in an amount of between about 10 and 100 moles of ligand per gram atom of said rhodium.

11. The process according to claim 10 wherein said rhodium catalyst is employed in said liquid reaction medium in an amount of from about 10 ppm to 500 ppm rhodium, calculated as the metal.

12. A process for hydroformylation of an internal olefin to form the corresponding aldehyde which comprises contacting an aliphatic internal olefin having from 4 to 20 carbon atoms per molecule in a hydroformylation reaction zone in the presence of $H_2$ and CO and in the presence of a liquid reaction medium containing a rhodium organophosphine hydroformylation catalyst wherein said organophosphine comprises at least one tricycloalkylophosphine of the formula:

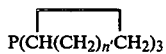

wherein "n" is an integer of 1 to 8, inclusive, at a total carbon monoxide and hydrogen pressure of from about 5,500 to 11,000 kPa and a reaction temperature of from about 80 to 200° C., a rhodium catalyst concentration of from about 10 ppm to 500 ppm rhodium, calculated as the metal, and at a tricycloalkyl phosphine ligand concentration of between about 10 and 100 moles of said ligand in said liquid reaction medium per gram atom of said rhodium.

* * * * *